(12) United States Patent
Lawrence et al.

(10) Patent No.: US 9,388,971 B2
(45) Date of Patent: Jul. 12, 2016

(54) METHOD FOR MAKING A LIGHT HANDLE COVER

(71) Applicant: Aspen Surgical Products, Inc., Caledonia, MI (US)

(72) Inventors: Robert J. Lawrence, Grand Rapids, MI (US); Ryan Severns, Plainwell, MI (US)

(73) Assignee: Aspen Surgical Products, Inc., Caledonia, MI (US)

( * ) Notice: Subject to any disclaimer, the term of this patent is extended or adjusted under 35 U.S.C. 154(b) by 41 days.

(21) Appl. No.: 14/286,086

(22) Filed: May 23, 2014

(65) Prior Publication Data
US 2014/0252680 A1    Sep. 11, 2014

Related U.S. Application Data

(62) Division of application No. 13/613,088, filed on Sep. 13, 2012, now Pat. No. 8,763,207.

(51) Int. Cl.
| | |
|---|---|
| *B29C 45/44* | (2006.01) |
| *F21V 21/40* | (2006.01) |
| *B29C 45/43* | (2006.01) |
| *A61B 17/00* | (2006.01) |

(52) U.S. Cl.
CPC ............. *F21V 21/40* (2013.01); *B29C 45/4407* (2013.01); *A61B 2017/00526* (2013.01); *A61B 2090/308* (2016.02); *B29C 45/43* (2013.01); *B29C 2045/4414* (2013.01); *Y10T 16/466* (2015.01)

(58) Field of Classification Search
CPC .................. B29C 2045/4414; B29C 45/4407; F21V 21/40–21/403
See application file for complete search history.

(56) References Cited

U.S. PATENT DOCUMENTS

| | | | | |
|---|---|---|---|---|
| 3,720,250 | A * | 3/1973 | Goldberg | B67B 7/92 150/154 |
| 4,125,246 | A * | 11/1978 | Von Holdt | B29C 45/0017 249/144 |
| 4,541,795 | A * | 9/1985 | Cole | B29C 45/4407 249/142 |
| 4,605,124 | A * | 8/1986 | Sandel | A61B 19/081 16/421 |
| D298,864 | S | 12/1988 | Jefferson | |
| 4,976,299 | A | 12/1990 | Bickelman | |
| 5,065,296 | A | 11/1991 | Cude | |
| 5,156,456 | A | 10/1992 | Hoftman et al. | |
| 5,465,461 | A | 11/1995 | Sandel | |
| 5,669,102 | A | 9/1997 | Sandel | |
| 5,884,996 | A | 3/1999 | Cottone et al. | |
| 6,447,149 | B1 | 9/2002 | Kaforey et al. | |
| 6,551,093 | B2 * | 4/2003 | Taha | B29C 45/262 425/556 |
| 7,757,352 | B2 | 7/2010 | Halamish et al. | |
| 2007/0051739 | A1 * | 3/2007 | Giraud | B29C 33/44 220/839 |
| 2014/0071701 | A1 | 3/2014 | Lawrence et al. | |

* cited by examiner

*Primary Examiner* — Jill Heitbrink
(74) *Attorney, Agent, or Firm* — Price Heneveld LLP (57) ABSTRACT

A method of making a light handle cover including providing a first mold tool and a second mold tool. The first mold tool engages with the second mold tool to form a mold cavity. The mold cavity is injected with a moldable material. The light handle cover is formed as a single integral piece with a substantially cylindrical grab portion that is circumscribed on one end by a substantially circular base shield. A plurality of teeth are formed in the light handle cover. Each of the plurality of teeth is separated by a space. The light handle cover is ejected from the second mold tool with a burst of air.

14 Claims, 7 Drawing Sheets

METHOD FOR MAKING A LIGHT HANDLE COVER

CROSS-REFERENCE TO RELATED APPLICATION

This application is a divisional of and claims priority to U.S. patent application Ser. No. 13/613,088, now U.S. Pat. No. 8,763,207, filed on Sep. 13, 2012, entitled "METHOD FOR MAKING A LIGHT HANDLE COVER," the entire disclosure of which is hereby incorporated herein by reference.

BACKGROUND OF THE INVENTION

The present invention generally relates to a light handle cover, and more particularly relates to a method for making a light handle cover.

SUMMARY OF THE PRESENT INVENTION

One aspect of the present invention includes a method of making a light handle cover including providing a first mold tool and a second mold tool. The first mold tool engages with the second mold tool to form a mold cavity. The mold cavity is injected with a moldable material. The light handle cover is formed as a single integral piece with a substantially cylindrical grab portion that is circumscribed on one end by a substantially circular base shield. A plurality of teeth are formed in the light handle cover. Each of the plurality of teeth is separated by a space. The light handle cover is ejected from the second mold tool with a burst of air.

Another aspect of the present invention includes a light handle cover for use on surgical light handles, the improvement including a cylindrical grab portion and a substantially circular shield portion integrally connected with the cylindrical grab portion. A plurality of teeth are spaced a predetermined distance apart and include a base and a distal end. A width of the base is larger than a width of the distal end and the distal end of the teeth define a circular handle receiving aperture.

Yet another aspect of the present invention includes a light handle cover having a substantially cylindrical grab portion defining an inner circumferential area and a base shield. A shoulder ring is disposed between and connects the substantially cylindrical grab portion with the base shield. A plurality of teeth extend inwardly from the inner circumferential area. Each of the plurality of teeth is separated by a space.

These and other aspects, objects, and features of the present invention will be understood and appreciated by those skilled in the art upon studying the following specification, claims, and appended drawings.

DETAILED DESCRIPTION OF EMBODIMENTS

Figure 1:
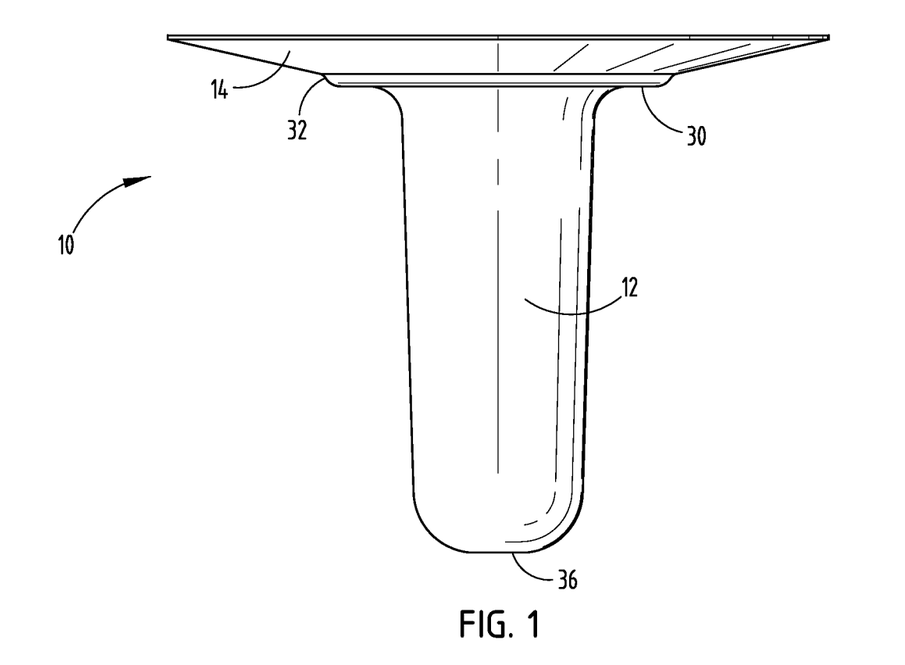
FIG. 1 is a side elevational view of a light handle cover of the present invention.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to FIGS. 1-16, reference numeral 10 generally designates a light handle cover for use on surgical light handles. The light handle cover 10 includes a cylindrical grab portion 12 and a substantially circular base shield 14 integrally connected with the cylindrical grab portion 12. A plurality of inwardly extending trapezoidally-shaped teeth 16 include a connecting end 18 and a distal end 20. A width of the connecting end 18 is larger than a width of the distal end 20. The distal end 20 of the teeth 16 define a circular handle receiving aperture 22.

Figure 2:
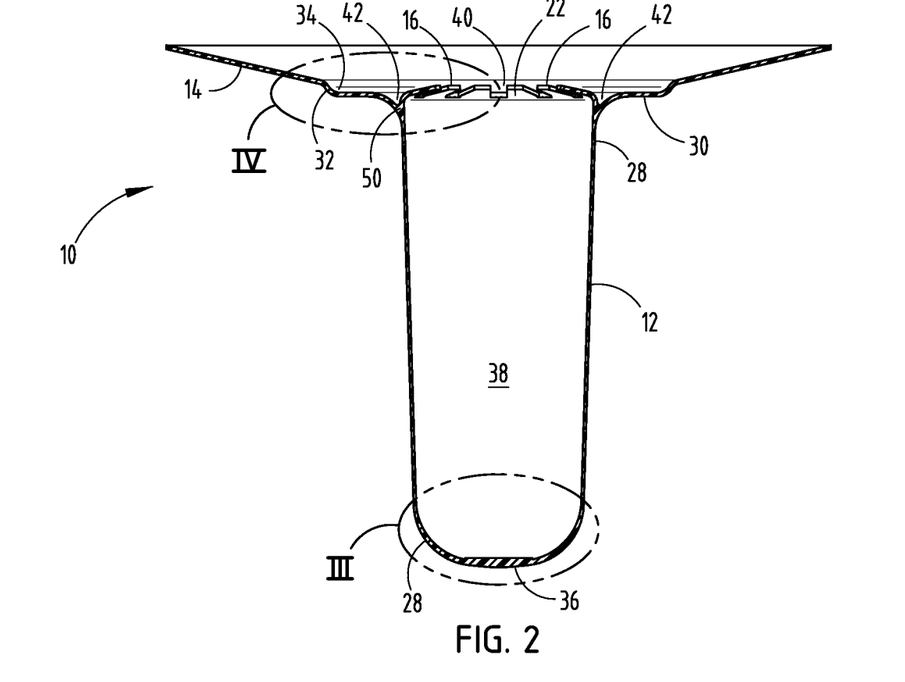
FIG. 2 is a side elevational cross-sectional view of the light handle cover of FIG. 1.
Figure 3:
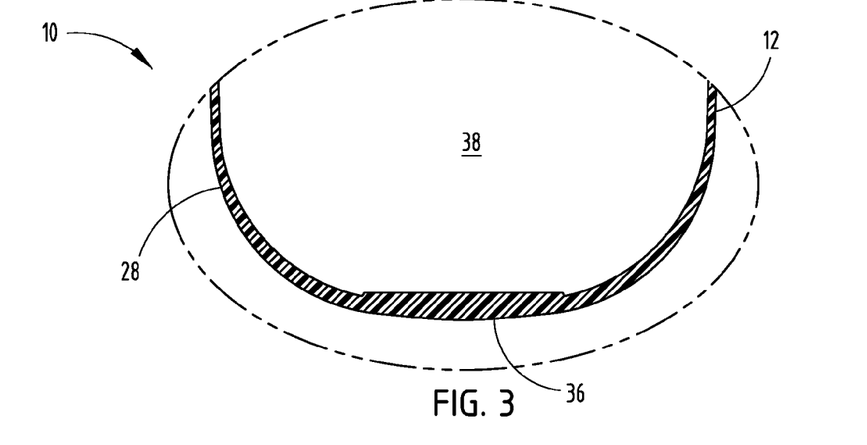
FIG. 3 is an enlarged partial cross-sectional view of a rounded distal end of the light handle cover of FIG. 2.

Referring now to FIGS. 1-3, the base shield 14 is configured to minimize the potential for contact between a hand of a user and a lighting device, such as a surgical light, used during surgery. The base shield 14 is circular in nature and slightly concave. The base shield 14 includes a shoulder ring 30 that extends around the grab portion 12 concentrically aligned with the base shield 14. The grab portion 12 is defined by a cylindrical wall 28 and extends from a center area of the base shield 14 substantially normal to the planar extent of the shoulder ring 30. The shoulder ring 30 defines a protruding portion 32 proximate the grab portion 12 and an annular recess 34 proximate the teeth 16. The shoulder ring 30, and consequently the annular recess 34, is generally configured to cover any exposed sharp gate edges that may occur during the molding process when the light handle cover 10 is being formed. The exposed sharp gate edges can potentially rip a latex glove or cut an individual that is installing the light handle cover 10 onto a surgical light handle. The grab portion 12 includes a rounded end 36 that may include a thickened wall section (FIG. 3). The grab portion 12 includes a substantially rounded distal end (FIG. 3). The grab portion 12 includes a handle receiving cavity 38 adapted to receive a surgical light handle to maintain a safe sterile environment during surgery.

Figure 4:
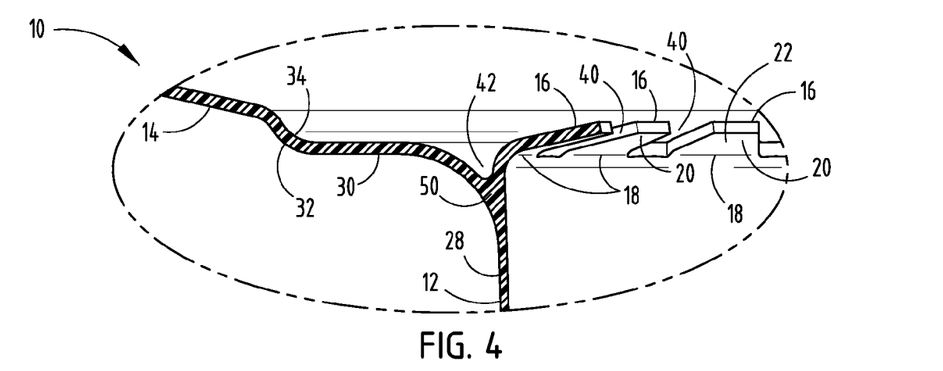
FIG. 4 is a side elevational cross-sectional view of teeth of the light handle cover of FIG. 2.
Figure 5:
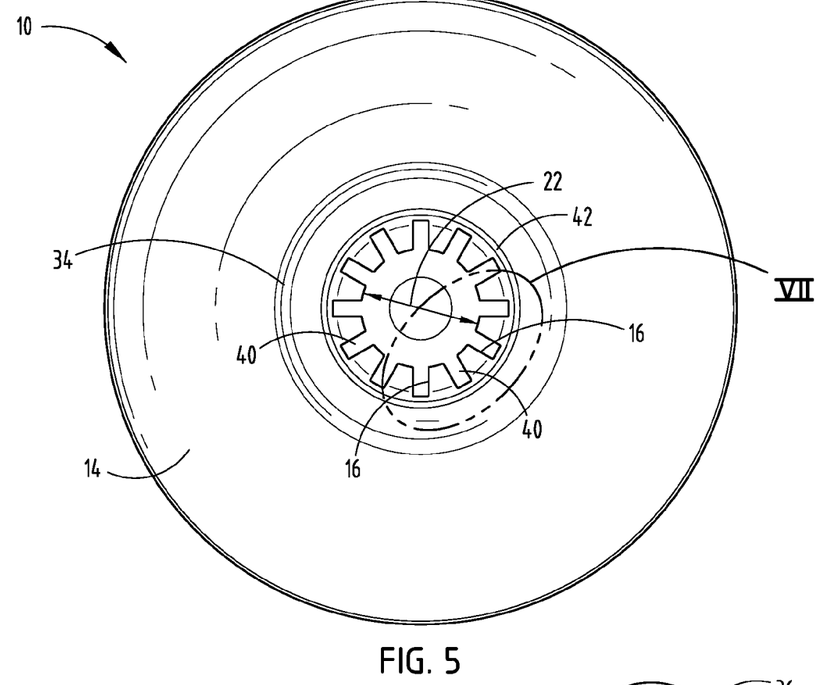
FIG. 5 is a bottom plan view of the teeth of the light handle cover of FIG. 4.
Figure 6:
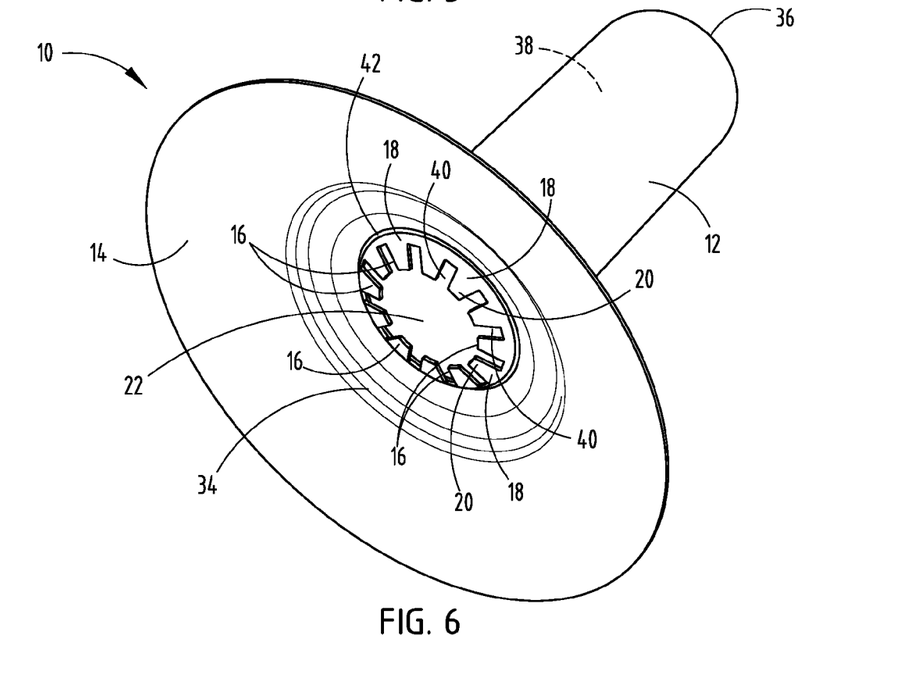
FIG. 6 is a bottom perspective view of the teeth of the light handle cover of FIG. 5.
Figure 7:
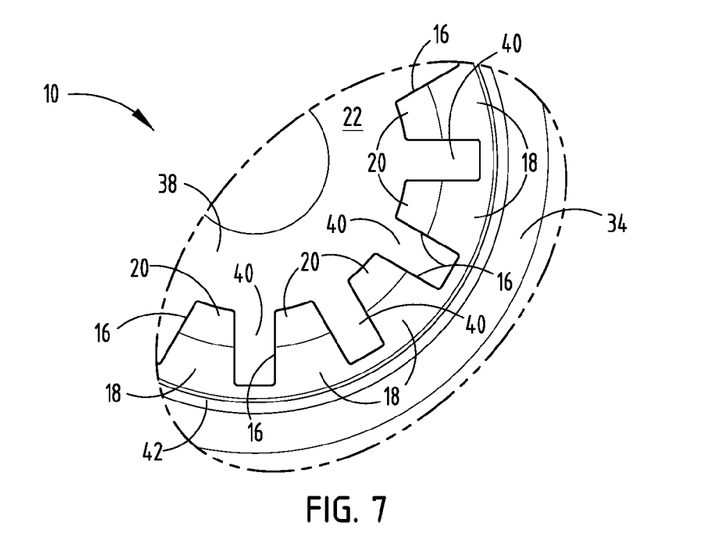
FIG. 7 is an enlarged elevational view of the teeth of the light handle cover of FIG. 5 with a substantially frustum-type construction.
Figure 8:
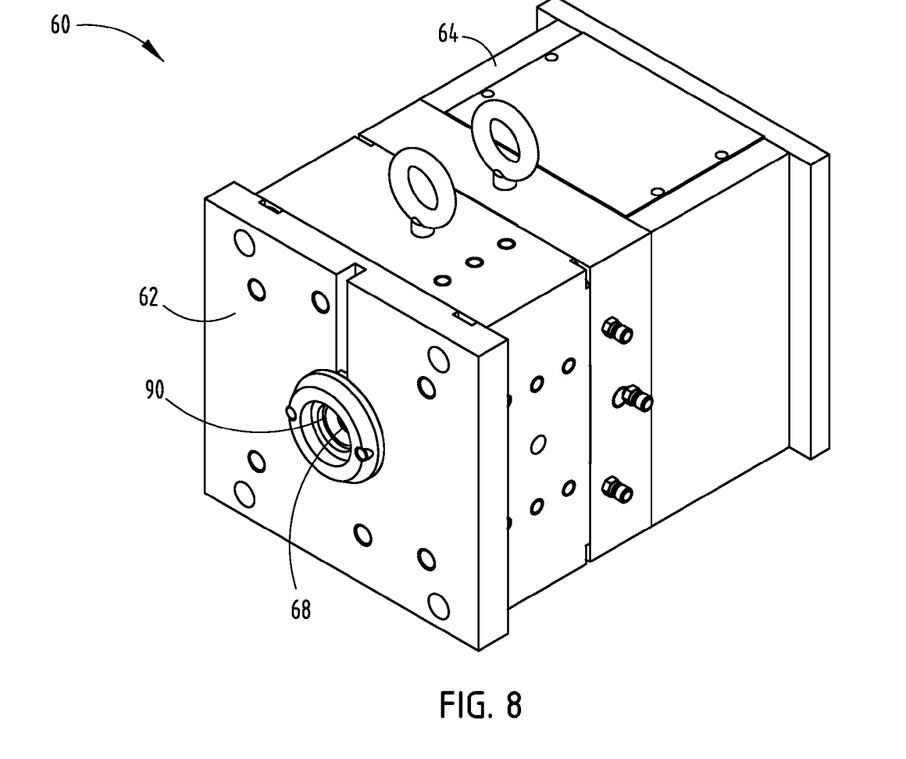
FIG. 8 is a side perspective view of an injection molding tool of the present invention.
Figure 9:
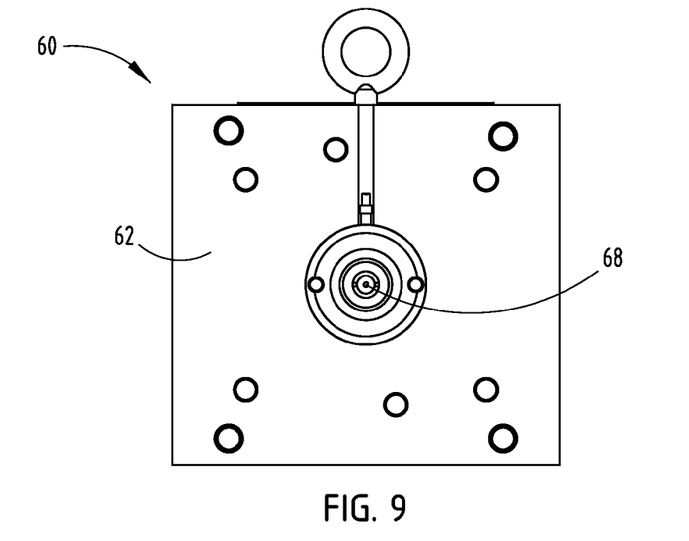
FIG. 9 is a front elevational view of the injection molding tool of FIG. 8.
Figure 10:
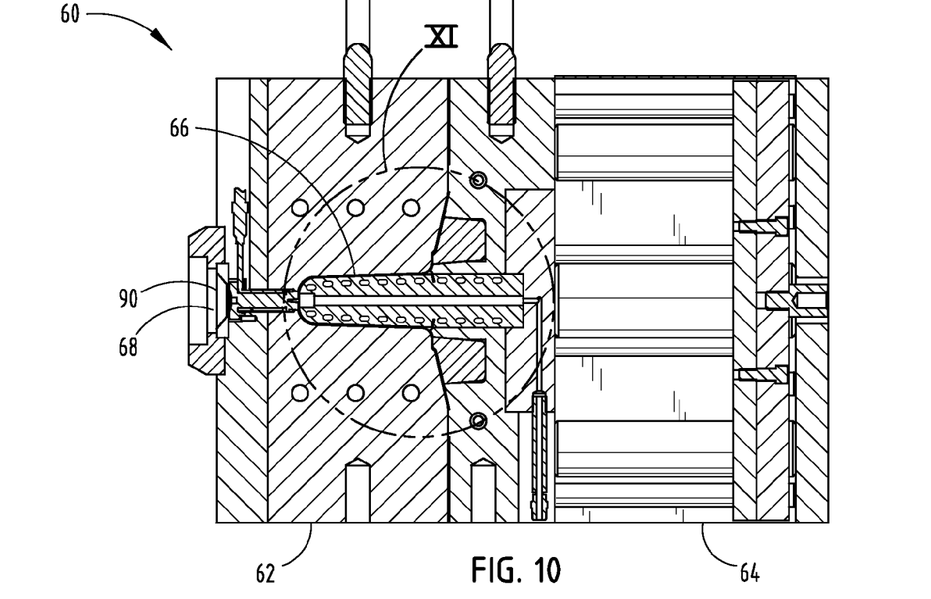
FIG. 10 is a side elevational cross-sectional view of a core of the injection molding tool of FIG. 8.
Figure 11:
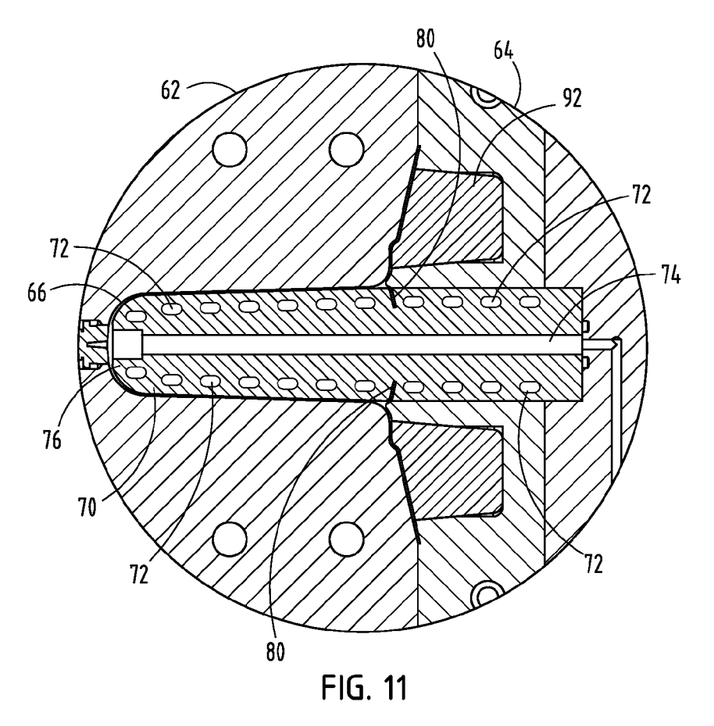
FIG. 11 is an enlarged side elevational cross-sectional view of area XI of FIG. 10.
Figure 12:
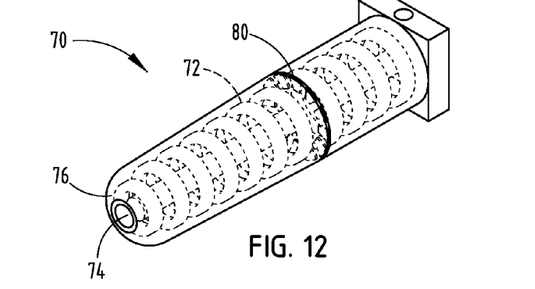
FIG. 12 is a top perspective view of a core of the injection molding tool of FIG. 8.
Figure 13:
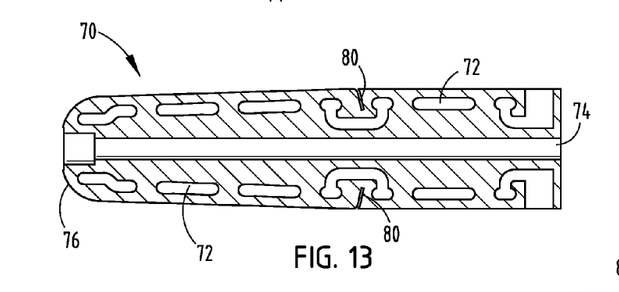
FIG. 13 is a top plan cross-sectional view of the core of FIG. 12.
Figure 14:
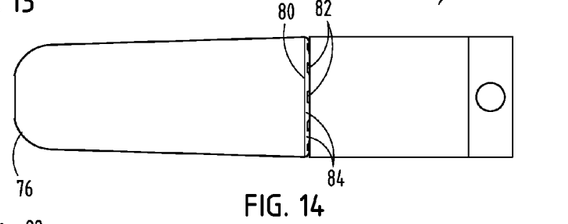
FIG. 14 is a top plan view of the core of FIG. 12.
Figure 15:
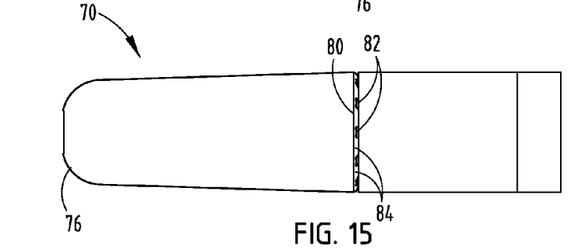
FIG. 15 is a side elevational view of the core of FIG. 12.
Figure 16:
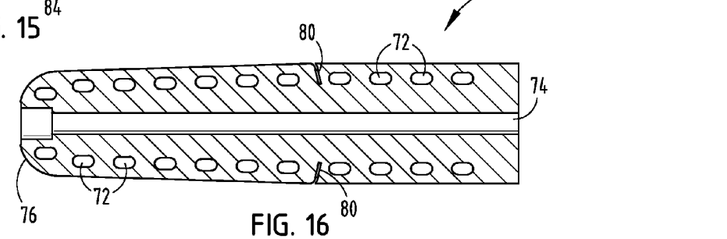
FIG. 16 is a side elevational cross-sectional view of the second mold half of FIG. 11 in the process of ejecting the light handle cover of the present invention.

Referring now to FIGS. 4-7, an underside of the light handle cover 10 includes the plurality of inwardly extending trapezoidally-shaped teeth 16 separated by a predetermined space 40. The teeth 16, grab portion 12, and base shield 14 are all integrally formed in one solid piece of material during an injection molding process, as disclosed in greater detail herein, and are not formed separately. The teeth 16 are flexible, but maintain a desired level of rigidity to secure the grab portion 12 to the surgical light handle. The spaces 40 between the teeth 16 are uniform and configured such that the teeth 16 do not contact one another, both when the light handle cover 10 is installed on a surgical light handle and when the light handle cover 10 is uninstalled. As illustrated in FIGS. 4 and 7, the teeth 16 are spaced approximately 0.125 inches (3.175 mm) from one another. The teeth 16, as illustrated, are approximately 0.230 inches long from the connecting end 18 to the distal end 20. Each of the teeth 16 extend radially inwardly and generally define the handle receiving aperture 22 that is substantially circular in shape. A circular channel 42 is disposed around the teeth 16. The channel 42 is generally defined between the connecting end 18 of the teeth 16 and the annular recess 34. Additionally, the distal end 20 of each of the teeth 16 has a width that is equal to or slightly larger than the width of the adjacent space 40. Moreover, with few exceptions, the entire light handle cover 10 maintains a substantially uniform thickness throughout the light handle cover 10.

Referring again to FIG. 4, as illustrated, the teeth 16 of the light handle cover 10 taper slightly away from the rounded end 36 of the light handle cover 10. The distal end 20 of each of the teeth 16 is substantially laterally aligned with the annular recess 34 of the light handle cover 10. The alignment of the teeth 16 and annular recess 34 provides a strong light handle cover 10 adapted to secure the surgical light handle. Notably, where the teeth 16 merge with the cylindrical wall 28 of the grab portion 12, a thickened area of material 50 is provided.

Referring again to FIGS. 5 and 6, as illustrated, there are twelve teeth 16 equidistantly spaced about the circular handle receiving aperture 22 defined by the grab portion 12. As noted above, each of the teeth 16 are spaced from adjacent teeth 16, such that the teeth 16 do not contact one another at any time during installation onto or removal from the surgical light handle. Additionally, as will be understood by one having ordinary skill in the art, during insertion of the light handle cover 10 onto the surgical light handle, the teeth 16 are flexed inward into the handle receiving cavity 38 defined by the grab portion 12 of the light handle cover 10. Upon removal of the surgical light handle from the handle receiving cavity 38, the teeth 16 once again taper outwardly away from the rounded end 36.

Referring now to FIGS. 8-11, the light handle cover 10 is manufactured using an injection molding tool 60. The injection molding tool 60 includes first and second mold halves 62, 64 that together define a mold cavity 66 (FIG. 10) disposed therebetween. The mold cavity 66 is configured to receive heated viscous molding material and, under high pressure, form a light handle cover shape that is cooled to form a light handle cover 10. The first mold half 62 includes an injection port or sprue 68 for receiving the molding material.

Referring now to FIGS. 12-16, a core 70 is disposed between the first and second mold halves 62, 64 and includes conformal cooling lines 72 that help to rapidly cool the molding material after the molding material has been injected into the mold cavity 66 and the injection molding process has been initiated. The core 70 includes an air duct 74 that extends through a center portion of the core 70, and is configured to channel a blast of air to an end 76 of the core 70, thus ejecting a finished light handle cover 10 from the injection molding tool 60 after the molding material has cooled and the light handle cover 10 has been formed. An ejection ring can be used to eject the light handle cover 10 from the injection molding tool 60, as discussed herein. The injection molding tool 60 is then available to mold another light handle cover 10.

The illustrated core 70 includes an annular slot 80 that defines the teeth 16 of the light handle cover 10. The annular slot 80 includes twelve abutments 82 that define the spaces 40 between the teeth 16 during the molding process. Voids 84 between the abutments 82 define the teeth 16 during the molding process. It will be understood by a person having ordinary skill in the art that any number of abutments 82 may be present to mold any number of teeth 16 in the light handle cover 10.

One method of making a light handle cover 10 generally includes providing the first mold half 62 and the second mold half 64, and coupling the first mold half 62 with the second mold half 64. An injection molding gate 90 (FIGS. 8 and 10) of the first mold half 62 is engaged with a molding material line that supplies molding material to the injection molding tool 60 under high pressure. As the molding material flows into the first mold half 62, the molding material fills the mold cavity 66 defined between the first mold half 62 and the second mold half 64. In addition, the molding material extends into a portion of the core 70. The conformal cooling lines 72 in the core 70 are filled with cooling material to quickly cool the molding material as the molding material is injected into the core 70. After a predetermined time of cooling, the first mold half 62 and the second mold half 64 are separated and the air duct 74 is injected with a blast of air, which dislodges the light handle cover 10 from the second mold half 64. At the same time, an ejection ring 92 (FIG. 11) disposed proximate the base shield 14 pushes the base shield 14, and consequently the entire light handle cover 10 outward, ejecting the light handle cover 10 from the second mold half 64. The first mold half 62 and the second mold half 64 are then coupled once again and available for receiving additional molding material to create subsequent light handle covers 10. As an example, the molding material may consist of polyethylene, low-density polyethylene, such as Lyondell-Basell Petrothene® NA27001, an ethylene-based softening agent, such as ExxonMobil EXACT™ 4049 Plastomer, and a polyethylene-based colorant. Further, the low-density polyethylene may be of various grades, depending on the applied use.

Figure 17:
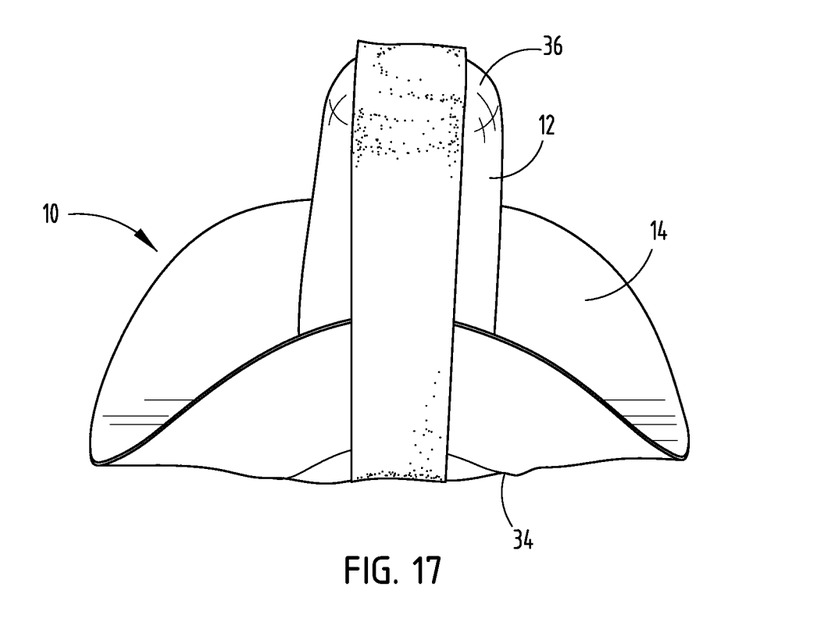
FIG. 17 is a top perspective view of a light handle cover after banding.
Figure 18:
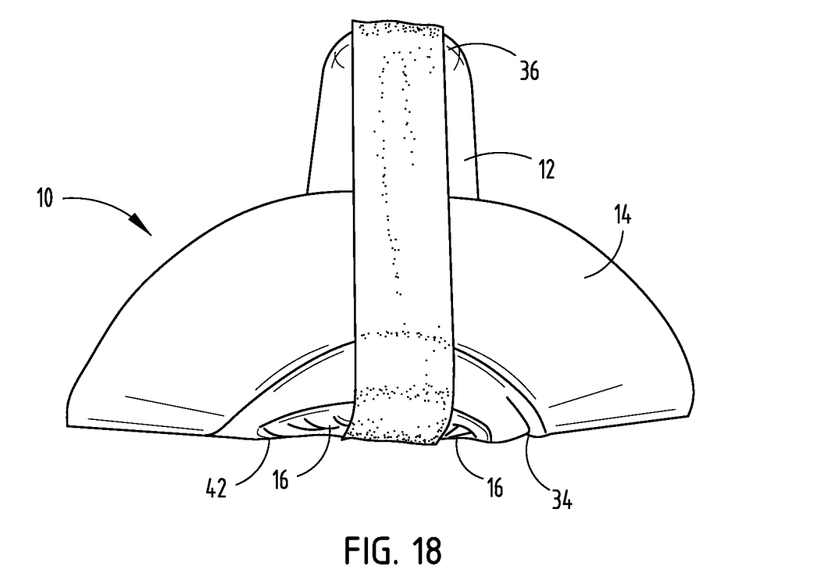
FIG. 18 is a bottom perspective view of a light handle cover after banding.

The light handle cover 10 may be bound as illustrated in FIGS. 17 and 18 for purposes of shipping. As a result of the material type and product size, the base shield 14 has a tendency to re-enter its original shape, as illustrated in FIGS. 1 and 2. Accordingly, the light handle cover 10 includes memory characteristics, such that bending or distortion of the light handle cover 10 is unlikely to ultimately result in deformation or destruction of the light handle cover 10. Moreover, as a result of the injection molding process, the teeth 16 are concentrically-aligned with the handle. Stated differently, the injection molding process prevents misalignment of the teeth 16 relative to the handle, which typically occurs during welding operations of grab portions 12 relative to the teeth 16 in traditional light handle covers. When the teeth 16 and the handle are misaligned, installation onto a light handle is difficult and can result in malfunctioning of the part.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. A method of making a light handle cover comprising:
providing a first mold tool;
providing a second mold tool;
engaging the first mold tool with the second mold tool to form a mold cavity;
injecting the mold cavity with a moldable material;
forming the light handle cover as a single integral piece with a substantially cylindrical grab portion that is circumscribed on one end by a substantially circular base shield;
forming a shoulder about the grab portion, the shoulder and grab portion coupled at a first transition portion defining a first radius;
coupling the base shield with the shoulder at a second transition portion defining a second radius;
forming a plurality of teeth in the light handle cover, each of the plurality of teeth separated by a space; and
ejecting the light handle cover from the second mold tool with a burst of air.

2. The method of claim 1, further comprising:
forming a rounded end on the grab portion, wherein the rounded end includes a thickened wall section.

3. The method of claim 1, further comprising:
forming a shoulder ring between the base shield and the light handle cover.

4. The method of claim 1, further comprising:
forming an annular recess on the base shield extending beyond the plurality of teeth.

5. The method of claim 4, further comprising:
forming a circular channel proximate the annular recess.

6. The method of claim 2, further comprising:
forming the teeth such that the teeth extend inwardly and away from the rounded end of the grab portion.

7. The method of claim 1, further comprising:
forming an annular recess on the base shield, wherein the annular recess projects towards a rounded end of the grab portion.

8. The method of claim 1, further comprising:
forming a circular channel between the annular recess and a connecting end of the teeth.

9. A method of making a light handle cover comprising:
injection molding a substantially cylindrical grab portion defining an inner circumferential area and a base shield;
injection molding a shoulder ring between the substantially cylindrical grab portion with the base shield; and
forming a first rounded transition portion between the shoulder ring and the grab portion;
forming a second rounded transition portion between the shoulder ring and the base shield; and
forming a plurality of teeth that extend inwardly from the inner circumferential area, each of the plurality of teeth separated by a space.

10. The method of claim 9, further comprising:
forming a rounded end on the substantially cylindrical grab portion, wherein the rounded end includes a thickened wall section.

11. The method of claim 9, further comprising:
defining an annular recess on the base shield.

12. The method of claim 9, further comprising:
forming a circular channel proximate the annular recess.

13. The method of claim 9, wherein each of the plurality of teeth extend at least partially away from a rounded end of the substantially cylindrical grab portion.

14. A method of making a light handle cover comprising:
providing a cylindrical grab portion having a distal end defining a handle receiving cavity and a central axis;
integrally connecting a shoulder ring with the cylindrical grab portion, the shoulder ring extending in a plane substantially orthogonally from the central axis;
integrally connecting a substantially circular base shield with the shoulder ring;
forming an annular recess in the cylindrical grab portion;

providing a plurality of teeth spaced a predetermined distance apart, the teeth including a base and a distal end, wherein a width of the base is larger than a width of the distal end and the distal end of the teeth define a circular handle receiving aperture;
directing the plurality of teeth projecting inwardly toward the handle receiving cavity and also away from the distal end of the cylindrical grab portion prior to engagement with the surgical light handle; and
defining a circumferential channel between a connecting end of the teeth and the annular recess.

* * * * *